US012324708B2

(12) United States Patent
Duong

(10) Patent No.: US 12,324,708 B2
(45) Date of Patent: Jun. 10, 2025

(54) AUGMENTED REALITY DENTAL SURGERY

(71) Applicant: Derek Duong, Costa Mesa, CA (US)

(72) Inventor: Derek Duong, Costa Mesa, CA (US)

( * ) Notice: Subject to any disclaimer, the term of this patent is extended or adjusted under 35 U.S.C. 154(b) by 884 days.

(21) Appl. No.: 17/177,446

(22) Filed: Feb. 17, 2021

(65) Prior Publication Data

US 2022/0257332 A1 Aug. 18, 2022

(51) Int. Cl.
*A61B 90/00* (2016.01)
*A61B 34/20* (2016.01)

(52) U.S. Cl.
CPC .............. *A61B 90/36* (2016.02); *A61B 34/20* (2016.02); *A61B 90/39* (2016.02); *A61B 2034/2057* (2016.02); *A61B 2034/2065* (2016.02); *A61B 2034/2068* (2016.02); *A61B 2090/365* (2016.02); *A61B 2090/3937* (2016.02); *A61B 2090/3966* (2016.02); *A61B 2090/3983* (2016.02)

(58) Field of Classification Search
None
See application file for complete search history.

(56) References Cited

U.S. PATENT DOCUMENTS

| | | | |
|---|---|---|---|
| 9,955,140 B2 | 4/2018 | Rhemann et al. | |
| 10,127,727 B1 * | 11/2018 | Yuan | G06F 3/013 |
| 10,194,131 B2 | 1/2019 | Casas | |
| 10,204,262 B2 | 2/2019 | Price et al. | |
| 10,326,975 B2 | 6/2019 | Casas | |
| 10,405,927 B1 | 9/2019 | Lang | |
| 10,535,151 B2 | 1/2020 | Bleyer et al. | |
| 10,656,731 B2 | 5/2020 | Garcia et al. | |
| 10,663,729 B2 | 5/2020 | Kazansky et al. | |
| 2010/0287485 A1 * | 11/2010 | Bertolami | G06F 3/011 715/764 |
| 2013/0172731 A1 * | 7/2013 | Gole | A61B 6/506 600/424 |
| 2016/0071238 A1 * | 3/2016 | Kimura | G06T 7/33 348/36 |
| 2016/0093108 A1 * | 3/2016 | Mao | G02B 27/017 345/633 |
| 2016/0154620 A1 | 6/2016 | Tsuda | |
| 2016/0324598 A1 * | 11/2016 | Bothorel | G03B 42/026 |

(Continued)

OTHER PUBLICATIONS

Chheang et al., "Collaborative virtual reality for laparoscopic liver surgery training," 2019 IEEE International Conference on Artificial Intelligence and Virtual Reality (AIVR), pp. 1-8 (Year: 2019).*

(Continued)

*Primary Examiner* — Anh-Tuan V Nguyen

(57) ABSTRACT

Systems and methods of the present disclosure relate to augmented reality (AR) assisted surgery. A system comprises a spatial virtual surgical treatment plan (SVSTP) for mixed or virtual reality; multiple AR interfaces (ARIs), each ARI configured to overlay the SVSTP onto a surgical site, wherein the ARIs are positioned at different angles to provide an unobstructed view of the surgical site and reduce parallax and occlusion errors during surgery, wherein the ARIs are configured to exchange coordinate information with each other such that the SVSTP viewed from each ARI is overlaid upon the surgical site and superimposed with each other to guide a surgical instrument.

20 Claims, 11 Drawing Sheets

(56) References Cited

U.S. PATENT DOCUMENTS

| | | |
|---|---|---|
| 2017/0172381 A1 | 6/2017 | Morimoto |
| 2017/0258526 A1* | 9/2017 | Lang ................... A61B 17/1742 |
| 2018/0070115 A1* | 3/2018 | Holmes ................ H04M 11/085 |
| 2018/0168781 A1* | 6/2018 | Kopelman ............. A61B 90/36 |
| 2018/0285052 A1* | 10/2018 | Eade .................... B65G 1/0492 |
| 2019/0005848 A1* | 1/2019 | Garcia Kilroy ........ G09B 23/28 |
| 2019/0025587 A1 | 1/2019 | Osterhout et al. |
| 2019/0056791 A1* | 2/2019 | Holz .................. G02B 27/0172 |
| 2019/0080515 A1* | 3/2019 | Geri ........................ G06F 3/012 |
| 2019/0095589 A1* | 3/2019 | Kim ....................... G16H 10/60 |
| 2019/0114802 A1* | 4/2019 | Lazarow ............. H04W 56/001 |
| 2019/0385370 A1* | 12/2019 | Boyapalle ............... G06F 3/012 |
| 2020/0014855 A1* | 1/2020 | Blanquart .......... A61B 1/00183 |
| 2020/0054398 A1* | 2/2020 | Kovtun .................. G16H 40/63 |
| 2020/0105068 A1 | 4/2020 | Panse |
| 2020/0129136 A1 | 4/2020 | Harding |
| 2020/0167120 A1* | 5/2020 | Rakshit ................ H04L 67/131 |
| 2021/0015583 A1* | 1/2021 | Avisar ................... G06F 3/1454 |
| 2021/0350611 A1* | 11/2021 | Ishihara ................ G06T 19/006 |
| 2022/0028170 A1* | 1/2022 | Haapoja .................... G06T 7/70 |
| 2022/0207756 A1* | 6/2022 | Ren ....................... G06T 7/0002 |

OTHER PUBLICATIONS

International Search Report and Written Opinion for Application No. PCT/US2022/012722, dated Apr. 22, 2022.
ResearchGate, Journal of Oral Implantology, The Effects of a New Implant Abutment Design on Peri-Implant Soft Tissues,, Oct. 2014.
Poseido Journal, Kowalski, et al., Accuracy of Guided Osteotomy using Dental Implant Treatment-Planning Software in Combination with an Optical Scan of a Dental Cast, 2014.
BMC Oral Health, Pellegrino, et al., Augmented Reality for Dental Implantology: a pilot Clinical Report of two Cases, 2019.
BioHorizon's, Implant Clinical Review, Jan. 2012.
Tum, Study on Software Architectures for Augmented Reality Systems, Oct. 2002 and Jul. 2004.
BMC Medical Imaging, Vision-based Markerless Registration using Stereo Vision and an Augmented Reality Surgical Navigation System: a pilot study, Suenaga, et al., 2015.

* cited by examiner

AUGMENTED REALITY DENTAL SURGERY

BACKGROUND

Augmented reality (AR) may be used in an increasing number of applications including surgery, for example. While the use of AR may offer benefits, shortcomings may include image issues such as parallax errors and occlusions, and recalibrations due to movement of a tool or patient during a procedure. Other issues may include a surgeon's inability to reference a screen and an operative site simultaneously.

BRIEF DESCRIPTION OF THE DRAWINGS

These drawings illustrate certain aspects of some of the embodiments of the present disclosure and should not be used to limit or define the disclosure.

SUMMARY

Figure 1:
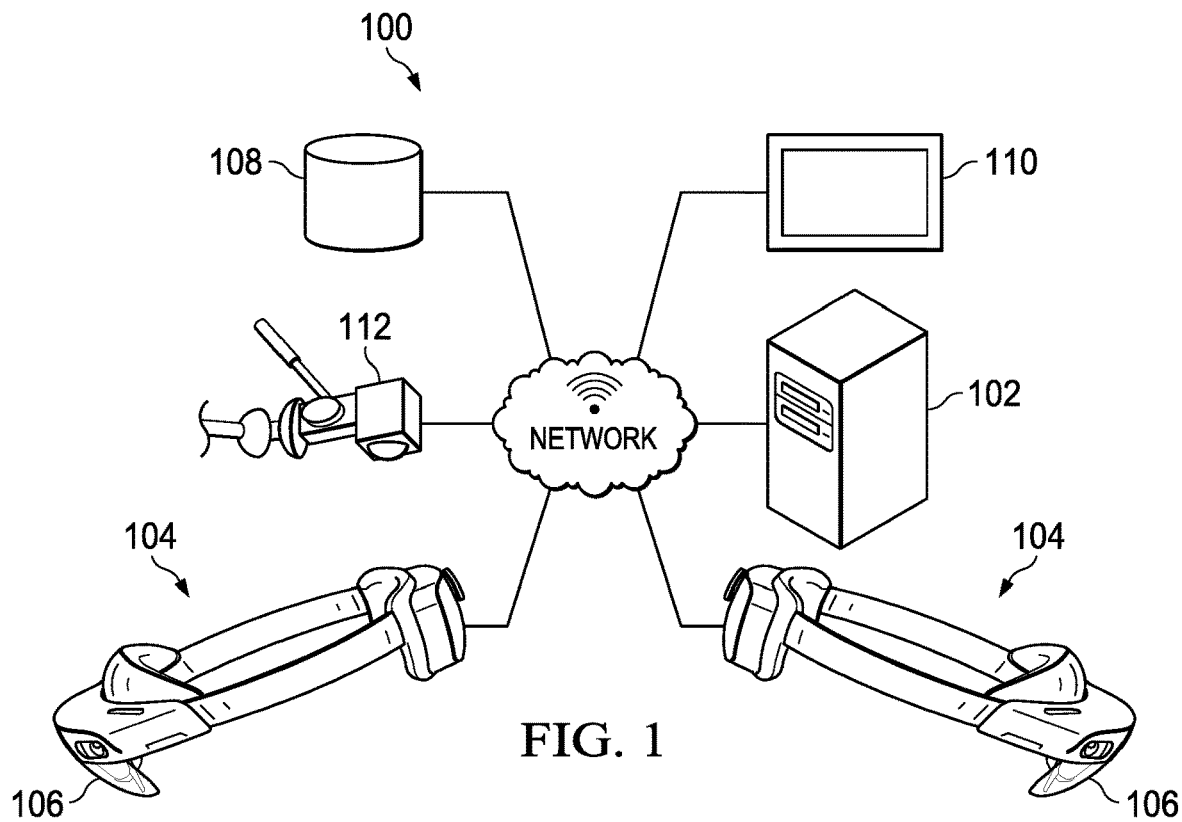
FIG. 1 illustrates an exemplary system for performing AR assisted procedures, in accordance with embodiments of the present disclosure.

Disclosed herein is an example of an AR assisted surgical system comprising: a spatial virtual surgical treatment plan (SVSTP) for mixed or virtual reality; multiple AR interfaces (ARIs), each ARI configured to overlay the SVSTP onto a surgical site, wherein the ARIs are positioned at different angles to provide an unobstructed view of the surgical site and reduce parallax and occlusion errors during surgery, wherein the ARIs are configured to exchange coordinate information with each other such that the SVSTP viewed from each ARI is overlaid upon the surgical site and superimposed with each other to guide a surgical instrument. It should be noted that additional ARIs provide additional viewing angles when observing the physical surgical instrument to prevent parallaxing and occlusion issues when guiding the surgeon to align a physical surgical instrument to the correct drilling angle and location.

Further disclosed herein is an example a method for performing augmented reality (AR) assisted surgery comprising: A method for performing augmented reality (AR) assisted surgery, the method comprising: loading a spatial virtual surgical treatment plan (SVSTP) onto multiple ARIs that are positioned at different angles to eliminate parallax and occlusion issues during surgery; identifying virtual and corresponding physical markers with each ARI based on the SVSTP without looking away from the surgical site; exchange coordinate information between the ARIs such that the SVSTP viewed from each ARI is overlaid upon the surgical site and superimposed with each other to guide a surgical instrument. Multiple ARIs overlaying the virtual image (SVSTP) to the patient's surgical site provides different view angles during the aligning of the physical surgical instrument (surgical hand-piece or osteotome) to prevent parallaxing and occlusion issues.

DETAILED DESCRIPTION

It is to be understood that the present disclosure is not limited to particular devices or methods, which may, of course, vary. It is also to be understood that the terminology used herein is for the purpose of describing particular embodiments only, and is not intended to be limiting. All numbers and ranges disclosed herein may vary by some amount. Whenever a numerical range with a lower limit and an upper limit is disclosed, any number and any included range falling within the range are specifically disclosed. Although individual embodiments are discussed herein, the invention covers all combinations of all those embodiments. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected. If there is any conflict in the usages of a word or term in this specification and one or more patent or other documents that may be incorporated herein by reference, the definitions that are consistent with this specification should be adopted for the purposes of understanding this invention.

Disclosed herein are techniques for performing surgical procedures utilizing augmented reality (AR). Surgical planning and aligning of a physical surgical instrument during an AR Smart Vision surgical procedure to prevent parallaxing issues by calibrating the physical surgical instrument from multiple ARIs at multiple angles but does not require the surgeon to look away from the surgical site. The ARI overlays a spatial virtual surgical treatment plan (SVSTP) on the patient's physical surgical site, enabling the surgeon to see the outline of a hidden view or occlusion view.

The SVSTP may include a virtual image that may include details of the physical surgical site and potential or planned surgical procedures. The SVSTP may include and/or display surgical site data such as CT, Mill, 3D, x-ray, CAD, and/or 3D Cone Beam data as well as CAD data of surgical tools. Coordinates of the SVSTP or details therein may be received by each ARI.

For example, the anchoring of the virtual image/SVSTP to selected physical marker(s) enables the SVSTP to overlay on the surgical site. As a result, the SVSTP of each ARI is precisely superimposed. Usage of these multiple angles may prevent or reduce occurrences of parallax errors and/or occlusions that may be encountered during surgical procedures.

In some examples, the surgical site (e.g., a patient) may be positioned between a first user (e.g., a surgeon) and a second user (e.g., an assistant). Each user may wear an AR interface (e.g., a headset). The AR interfaces (ARIs) may facilitate surgical procedures, as well as be used for demonstration or teaching purposes.

Non-limiting examples of the ARIs may include mixed reality smartglasses, head gears, and/or helmets that may each include a display for virtual images to be spatially viewed by the user. Each ARI may be configured to display virtual images including spatial representations of image details such as the SVSTP. The surgeon's ARI overlay the SVSTP on the surgical site. The Assistant's ARI overlay the SVSTP on the surgical site. Once that process is completed. The SVSTPs of the surgeon and the assistant are superimposed. In some examples, the ARIs may be in communication with a computer. In some examples, the physical markers may be rigid.

After transmitting/loading of the SVSTP onto each ARI, the surgeon may identify physical markers at the surgical site. The physical markers may allow for proper overlaying of the SVSTP onto the surgical site. In some examples, the physical markers may include teeth which are irregular in shape/size and are radio-opaque or captured by 3D x-ray. The physical markers may also include intra-oral anatomical landmarks such as bony tori which are also irregular in shape/size and radio-opaque or captured by 3D x-ray.

The physical markers may also include intra-oral anatomical landmarks such as bony tori which are also irregular in shape/size and radio-opaque or captured by 3D x-ray. The physical markers may also include inserted irregular shape radio-opaque screws to be used as physical rigid markers (in case of complete edentulous patient or partial edentulous where remaining teeth are not rigid enough to use as physical rigid markers).

In some examples, the physical rigid markers may include radiographic markers positioned at the surgical site (e.g., for patients without teeth). The radiographic markers may be utilized depending on whether the patient is full/partial dentition or a complete edentulous patient where irregularly shaped radiographic markers may be inserted surgically prior to taking a cone beam and/or x-ray, for example, to provide the SVSTP. The markers may be used as references to overlay virtual images onto the surgical site via the ARIs.

The surgeon may select, via his ARI, virtual markers on the SVSTP that correspond with the physical rigid markers at the surgical site. Additionally, the assistant may identify the same or different physical rigid markers at the surgical site. The overlaying of the SVSTP over the surgical site based on the selected physical rigid marker(s) creates a coordinate transformation matrix in the ARI(s). This coordinate transformation matrix will convert absolute position to relative position to exchange coordination information between the ARIs.

Each ARI may be operable to synchronize the assistant's coordinates with the surgeon's coordinates and vice versa via a coordinate transformation matrix. The synchronization of multiple ARIs at different view angles also allows the users to calibrate the physical surgical instruments such as a surgical hand-piece or osteotome and or subsequent placement of dental implant(s) from different angles to prevent parallaxing and occlusion issues. This provides AR surgical guidance to the surgeon to align physical surgical instrument such as a surgical hand-piece or osteotome and placement of dental implant(s) to the correct angle and location in the jaw.

The synchronization may assist in alignment of a physical surgical instrument to a CAD image of the surgical instrument in the virtual image. With the initial alignment of the SVSTP onto the physical surgical site of the patient, any subsequent locations and calculations may be relative to the SVSTP. To ensure precision during movement, the SVSTP may adjust to maintain precise alignment based on the selected physical markers with the surgical site in real time without lag. Specifically, the SVSTP may be dynamically overlaid upon the surgical site due to movement of a user of the ARI and/or movement of the surgical site (e.g., a patient) in real time.

Additionally, the SVSTP may be manipulated (e.g., dropping or drawing locations pins into the virtual image) to indicate locations for a surgical procedure (e.g., incision, dental implant target location, extraction, etc.), for example. Multiple ARI views with the loaded SVSTP must be aligned to physical markers to ensure that the virtual images (SVSTP) are precisely superimposed. Multiple ARIs angle views prevent parallaxing and occlusion issues when observing a physical surgical instrument or placement of dental implants.

During the virtual surgical planning in the SVSTP, the surgeon may move around the projected SVSTP from his ARI and move around the projected SVSTP in space to plan out the surgical procedure. Since the surgeon can walk around and observe the projected SVSTP, there is no parallax issue or occlusion issue.

FIG. 1 illustrates a network 100 in accordance with embodiments of the present disclosure. The network 100 may also be referred to as a system in some examples. The network 100 may include a computer 102 that is operable to communicate with at least one ARI 104. The ARI(s) 104 may include any suitable ARI such as, for example, mixed reality smartglasses, head gears, and/or helmets that may each include a display for virtual images to be spatially viewed by the user, as previously noted.

Each of the ARIs 104 may generate and/or position images in the user's field of view such as on a face shield 106 (a display). Each face shield 106 may have a height sufficient to protect a user's face and neck while allowing simultaneous spatial viewing of images displayed on the face shield 106 during a surgical procedure. In some examples, the face shield 106 may have a height ranging from 6 inches to 12 inches, and a width sufficient to cover the face and neck such as 8 inches to 16 inches for example.

The face shield 106 may extend to a user's chin or neck for protection. It should be noted that these dimensions are non-limiting and dimensions outside of these ranges may be utilized depending on a size of the user, for example.

Additionally, each ARI 104 may be operable to overlay, and/or manipulate the SVSTP on each face shield 106. Each ARI 104 may be further operable to access 3D model information (e.g., CAD) about dental surgical tools, implants, sleeves, and custom inserts which may be stored on the ARI 104 or on separate storage. Each ARI 104 may include a storage unit, and/or any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes.

Each ARI 104 may include a processing unit (e.g., microprocessor) that may process data by executing software or instructions obtained from a local non-transitory computer readable media. For example, each ARI 104 may include at least 24 digital signal processors (DSP) that can execute 1 trillion instructions per second (at least 50 times faster than a desktop computer).

The non-transitory computer readable media may store software or instructions of the methods described herein. Non-transitory computer readable media may include any instrumentality or aggregation of instrumentalities that may retain data and/or instructions for a period of time. The non-transitory computer readable media may include, for example, storage media as well as communications media such wires, optical fibers, microwaves, radio waves, and other electromagnetic and/or optical carriers; and/or any combination of the foregoing.

The overlaying of the SVSTP onto the surgical site based on the surgeon's and the assistant's selections may be performed by the ARI 104. The selections may be used as an indication of the surgeon's and assistant's tooth selection, for example.

Physical rigid markers are only inserted into a patient's jaw when the patient is missing all teeth, thus no rigid reference point present to use for later overlaying the SVSTP to the surgical site. Irregular shape and radio-opaque screws must then be inserted in the patient's jaw prior to taking 3D x-rays. In most cases, no physical rigid screw or markers needed to be inserted, the uniqueness shape of a tooth or teeth from each patient is sufficient to use as physical rigid marker(s). Inserted irregular shape radio-opaque screw or markers should be made of material that can be captured by 3D x-ray with a distinct irregular shape outline. This can also apply to a patient who has only few remaining few teeth (or partial edentulous) where the few remaining teeth are too loose or mobile due to periodontal disease, these teeth are not rigid enough to allow to precise overlaying of the SVSTP to the surgical site. The surgeon then must insert the irregular and radio-opaque shape screw in the jaw prior to taking the 3D x-ray to allow for overlaying process of the SVSTP to the surgical site. Radio-opaque markers may be inserted or installed on the patient prior to taking 3D x-ray. These radio-opaque markers provide the surgeon to plan the implant positions or location prior to surgery. Similarly, in AR dental surgery, for a patient without any teeth, physical rigid markers that are irregular in shape and radio-opaque must be inserted prior to taking 3D x-ray to provide reference for surgical planning in SVSTP and later use for aligning the SVSTP to the patient's physical surgical site.

A computer 102 may synchronize the coordinates between the AR devices 104 and distribute/update the coordinates between the AR devices 104 to align a physical surgical instrument to a CAD image of the instrument in the SVSTP. The computer 102 may also store or be operable to access 3D model information (e.g., CAD files) about dental surgical tools, implants, sleeves, and custom inserts which may be stored on the computer or on separate storage. The computer 102 may exchange coordinates of viewed objects between the ARIs 104. The computer 102 may include a display, a storage unit, and/or any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, the computer 102 may include a network storage device, or any other suitable device. The computer 102 may include a processing unit (e.g., microprocessor) that may process data by executing software or instructions obtained from a local non-transitory computer readable media (e.g., optical disks, magnetic disks). The non-transitory computer readable media may store software or instructions of the methods described herein. Non-transitory computer readable media may include any instrumentality or aggregation of instrumentalities that may retain data and/or instructions for a period of time. The non-transitory computer readable media may include, for example, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing. The computer 102 may also include input device(s) (e.g., keyboard, mouse, touchpad, etc.) and output device(s) (e.g., monitor, printer, etc.). The input device(s) and output device(s) provide a user interface. For example, the computer 102 may enable an operator to select and perform analysis, view collected data, view analysis results, and/or perform other tasks. A data repository 108 may also be in communication with the network for storing of data obtained with any components in communication with the network 100.

A device 110 may provide remote viewing of the surgical procedure where the users/observers/trainees may select the surgeon's or assistant's view. A camera 112 may also be utilized in some embodiments to capture images such as surgical sites and communicate captured images to other components in the network 100, for example. The camera 112 may be operable to communicate with the computer 102, the device 110, and/or the ARIs 104. The network 100 may also allow for dynamic camera positioning based on the surgeon's and the assistant's view to minimize camera obstruction. Camera 112 may or may not be utilized for real time tracking of patient head movement during surgery. In scenarios that may rely upon the camera, the camera 112 may be operable to transmit image information to the computer 102. The computer 102 may then manipulate the image and/or transmit coordinates to the ARIs 104.

Additionally, the network 100 may allow for spatial virtual planning (in addition to 3D planning) which may enable dentists (not CAD technicians) to interactively experiment with various surgical or implanting options in virtual or mixed reality. The surgeon can use virtual dental implant screws in virtual reality (VR) (from implant CAD file) or an actual dental implant screw in mixed reality to fit in the virtual surgical site during the surgical planning phase (SVSTP).

Multiple ARIs are used to assist the surgeon to align the physical surgical instrument (surgical hand-piece, osteotome) in according to the precise surgical position or location of the planned dental implant in the SVSTP. In order to do this, ARIs must be aligned to the common site (matching physical rigid markers in the SVSTP to the corresponding physical rigid markers at the surgical site) and their coordinates must be synchronized as described in FIG. 5, for example.

Figure 2:
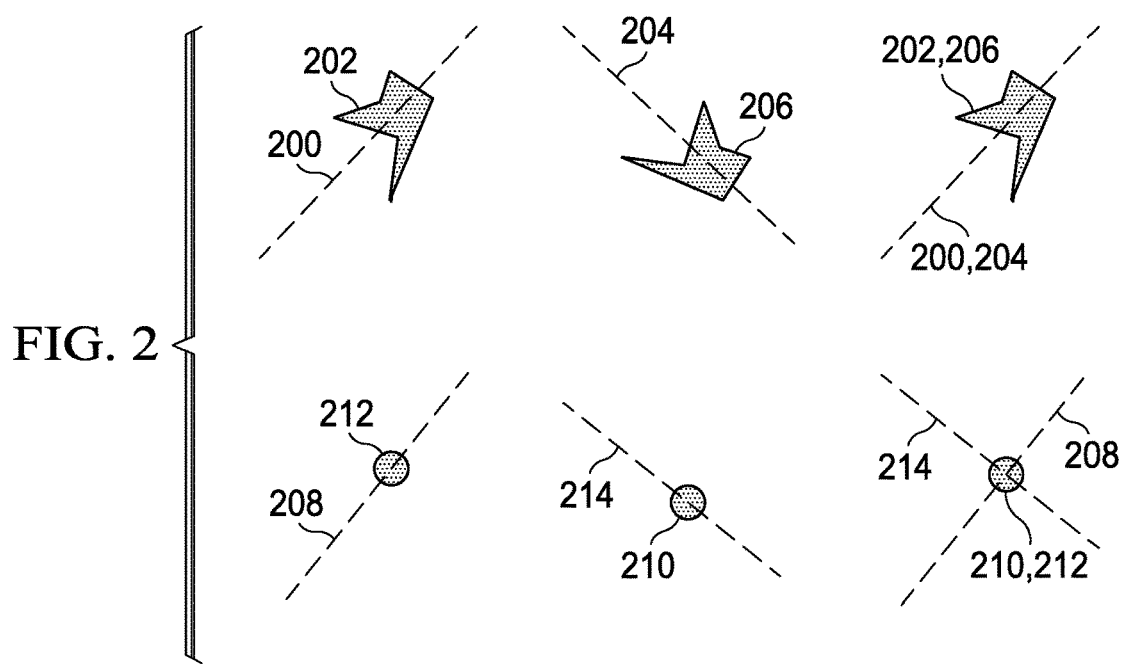
FIG. 2 illustrates physical markers such as irregular shape and radio-opaque markers that may be used in partial or complete edentulous patients where physical markers may be needed to insert surgically or non-surgically prior to obtaining 3D x-ray (e.g., cone beam, MRI, CT scan) for use in planning surgical procedures, and overlaying the spatial virtual surgical treatment plan (SVTP), precisely, to the patient's surgical site at the time of surgery for ARI dental implant or oral guided surgery, in accordance with embodiments of the present disclosure.

FIG. 2 illustrates physical markers 202 and 206 for image overlaying techniques, in accordance with particular examples of the present disclosure. The physical markers may be used in the overlaying process of the SVSTP to the patient's surgical site at the time of surgery, such as: a selected tooth or teeth, intraoral anatomical landmarks (bony tori), or inserted irregular shape radio-opaque screws to be used as physical rigid markers.

As illustrated, an orientation line 200 of the marker 202 may be accurately overlaid upon an orientation line 204 of the marker 206 due to the irregularity of the shapes of the markers, as opposed to orientation lines 208 and 210 of circular markers 212 and 214 that may not properly align due to the regular or circular shape of the markers 212 and 214.

The ARI 104 of the surgeon or assistant may select the same tooth (e.g., tooth #8) in the SVSTP/Cone beam/virtual image with same physical tooth of the patient (tooth #8). In this case, tooth #8 is an irregular shape physical rigid marker. The irregular shape on tooth #8 provide a distinct different contrast to allow the aligning of tooth #8 in the virtual image (SVSTP) to the patient tooth #8 at time of surgery. Therefore, the virtual image (SVSTP) is precisely aligned to the patient's surgical site.

Inserted irregular radio-opaque or radiographic screw are only used as physical rigid markers in complete edentulous or partial edentulous patient where references in the jaw are needed for planning in SVSTP and also for aligning corresponding markers from the SVSTP to the patient surgical site at time of surgery.

Subsequently, after the alignment, synchronization of multiple ARIs via the coordinate transformation matrix allows the surgeon to then calibrate the physical surgical instrument (surgical handpiece, osteotome) to the planned position or location of surgery according to the SVSTP without parallaxing or occlusion issues. Patients with adequate anchored teeth present, do not require inserted irregular radio-opaque or radiographic markers.

The coordinate transformation matrix is established in the ARI. The exchanging of coordinates between ARIs, occurs via a computer (e.g., server) where the computer transmits bytes (coordinates/not images) of information (small data information) to relaying ARIs. This process prevents a delaying or lagging effect that may occur when larger image information is being transferred which may not be safe in live surgical procedures.

Figure 3:
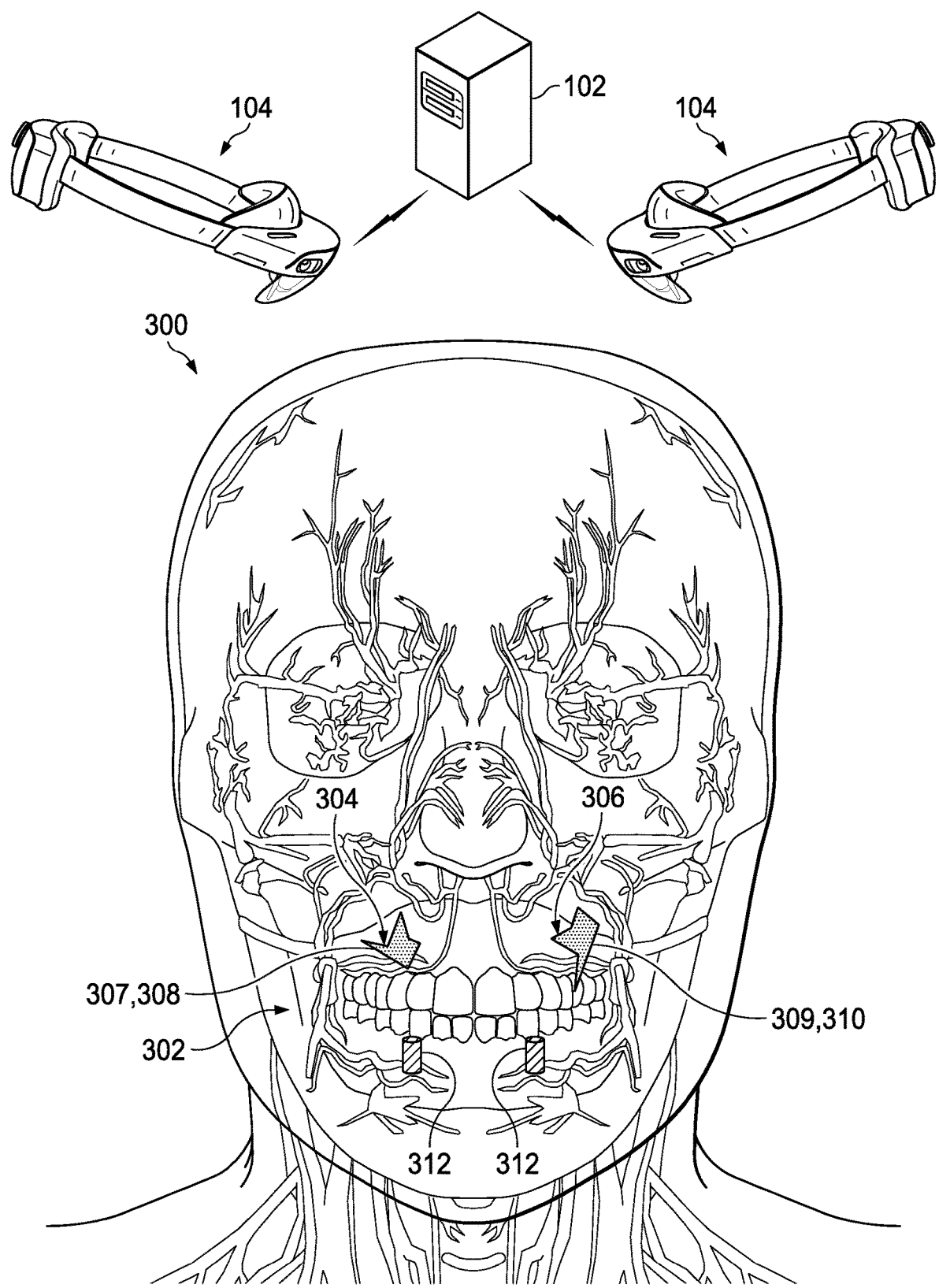
FIG. 3 illustrates the SVSTP superimposed upon a surgical site, in accordance with embodiments of the present disclosure.

FIG. 3 illustrates an SVSTP 300 (e.g., virtual image) overlay upon a surgical site 302, in accordance with particular examples of the present disclosure. A selection 304 may include a virtual marker 308 from the SVSTP that is overlaid upon a physical rigid marker(s) 307 at the physical surgical site 302. A selection 306 may include a virtual marker 310 that is overlaid upon a physical rigid marker(s) 309 at the physical surgical site 302. Coordinates of the selection 304 via a first ARI 104 may be transformed with coordinates of a selection 306 selected via a second ARI 104, and vice versa.

The assistant may select the same physical rigid marker(s) that the surgeon selects (e.g., tooth #8) or a different physical rigid marker(s) in the SVSTP (e.g., tooth #12). However, in some examples, the assistant's pre and post selection of the physical rigid marker(s) may be of the same tooth. For example, if the assistant selects tooth #8 which may be the same tooth selected by the surgeon, then the assistant may select the same tooth #8 at the patient's physical surgical site 302 in order for the ARI 104 to overlay the SVSTP 300 to the physical surgical site 302 precisely.

In other examples, the assistant may select tooth #12 in the SVSTP 300, which may be different from the surgeon's selected marker, the assistant may then select the same tooth #12 in the patient's physical surgical site in order for the ARI 104 to overlay the SVSTP 300 to the physical surgical site 302 precisely. This overlay may be performed autonomously, without user input, by the ARI 104, once the physical rigid markers are selected. Synchronization of the surgeon's coordinates with the assistant's coordinates eliminates parallaxing and/or occlusion.

The synchronization between users may occur via any suitable technique such as, for example, a coordinate transformation matrix. The different angle observations eliminate parallaxing and occlusion issues. The ARI 104 allows the SVSTP to be overlaid onto the patient's physical surgical site, enabling the surgeon to see the outline of a hidden view or occlusion view (e.g., superimposed outline of the SVSTP jawbone over patient's surgical site).

The selection 304 of the surgeon allows for the SVSTP 300 in his ARI to overlay on the surgical site. The selection 306 of the assistant allows for the SVTP in her ARI to overlay on the surgical site. The coordinate transformation matrix is created once the SVSTPs in the surgeon's ARI and the assistant's ARI overlay on the common surgical site. The overlaying of the virtual image/SVSTP of each ARI 104 over the common surgical area creates a coordinate transformation matrix (in ARIs). Once the surgeon and the assistant's ARIs completed the overlay process, the overlaid SVSTPs are precisely superimposed with each other and the ARIs pin the SVSTPs onto the surgical site. The precise superimposing of the SVSTPs allows the position (X,Y,Z) or (1, 2, 3) of the surgeon ARI to be transformed to the position (A, B, C) or (2.1, 1.4, 0.04) of the assistant. This allows the surgeon and the assistant(s)'s ARI observe the movement, location of the physical surgical instrument relative to the patient's planned surgical site in the SVSTP via transformation of coordinates between ARIs.

The overlaying of the SVSTP 300 to the surgical site is achieved by selecting virtual marker(s) in the SVSTP 300, which loaded to ARIs from the computer 102, to align with the corresponding physical rigid marker(s) of the patient surgical site. The selection to overlay the virtual marker(s) to the physical rigid marker(s) creates a coordinate transformation matrix in ARIs. The precise overlay of the SVSTP to the physical surgical site is achieved by the physical rigid marker(s) which was defined as a unique shape and radio-opacity of a tooth/teeth, inserted irregular shape radio-opaque screws, or irregular shape radio-opaque anatomical structure (tori). The precise superimposing of the SVSTPs of the multiple ARIs from multiple viewing angles, and the ARIs' coordinate exchange enables the guidance of the surgical instrument (dental handpiece, osteotome) to the correct vertical axis and location of the surgical site (planned implant position, lateral antrostomy etc.) minimizing if not eliminating parallaxing and occlusion issues.

To ensure precision during movement, the SVSTP 300 may adjust to maintain precise alignment and overlay with the surgical site 302. Specifically, the SVSTP 300 may dynamically overlay onto the surgical site 302 due to movement of a user of each ARI 104 and/or movement of the surgical site 302 (e.g., a patient).

In some examples, the SVSTP 300 may be interactive and manipulated (e.g., dropping or drawing locations pins 312 into the virtual image) to indicate locations for a surgical procedure (e.g., incision, dental implant target location, extraction, etc.), for example. This dynamic overlaying of the SVSTP 300 due to multiple viewing spatial views from multiple users may prevent or reduce instances of occlusion issues and/or parallax errors.

Figure 4:
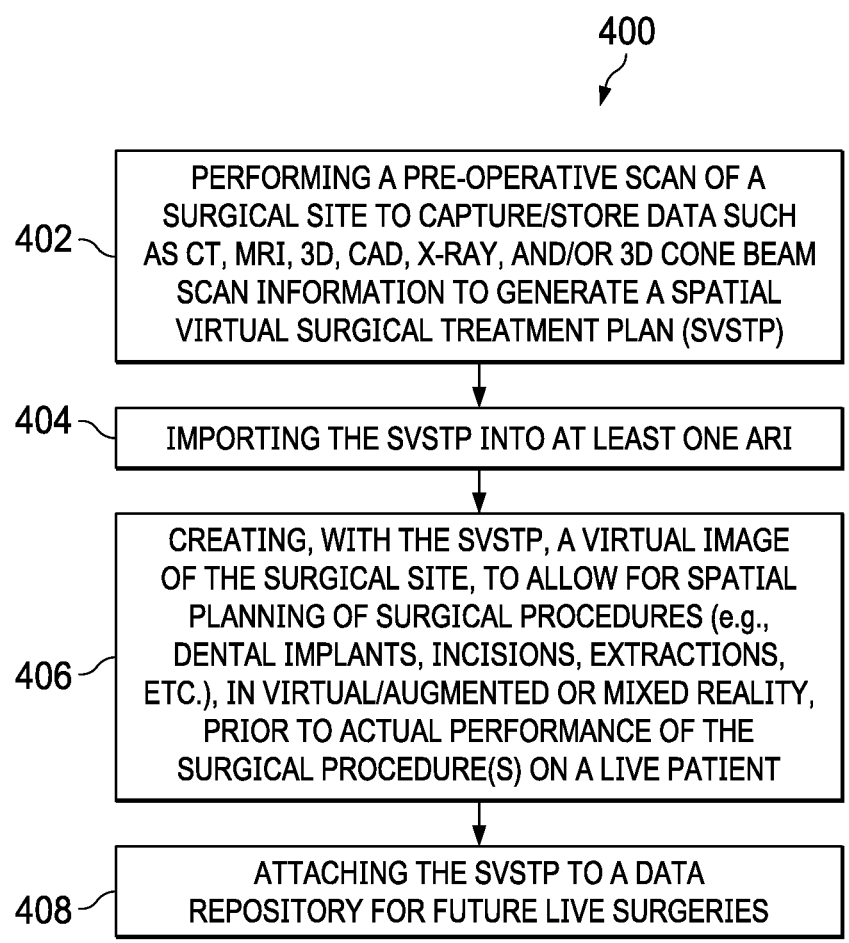
FIG. 4 illustrates flow sequence to create a spatial virtual surgical treatment plan (SVSTP), in accordance with embodiments of the present disclosure.

FIG. 4 illustrates a flow diagram 400 depicting an exemplary technique for generating the SVSTP for treating a patient, according to examples of the present disclosure.

At step 402, a pre-operative scan of a surgical site may be performed to capture and store information of the surgical site that may include bones, teeth, and/or soft tissue, within a mouth of a patient, for example. The information may include CT, MRI, 3D, x-ray, CAD information, and/or 3D Cone Beam data for inclusion in the SVSTP, for example. The 3D CAD information may include dental implants, osteotomy drills, or surgical instruments to be used in the SVSTP. In some examples, the SVSTP may be stored in a digital file(s) such as a DICOM file(s) (Digital Imaging and Communications in Medicine format). The computer 102 (e.g., as shown on FIG. 1) may store the SVSTP. During the SVSTP phase, there is 1 ARI (i.e., only the doctor or surgeon plans the surgery). No coordinate exchange is required.

At step 404, the SVSTP may be imported into at least one ARI. The importation may include coordinates. In some examples only coordinates may be exchanged between ARIs 104 and the computer 102 and similar devices on the network 100. Coordinate exchange may occur in bytes rather than megabytes (e.g., less than 1 MB) or gigabytes (e.g., less than 1 GB) or kilobytes (e.g., less than 1 KB) for systems that exchange images. These high data transfer systems may cause data latency resulting in lengthy set up or calibration during surgery.

In some examples, the SVSTP may employ dental implant planning software. It should be noted that in the SVSTP, the view for the surgeon may not be limited to a projected screen view; rather the view for the surgeon may be a projected spatial view of a 3-dimensional radiograph, for example.

At step 406, dental implant placement location(s) or surgical procedures (e.g., buccal, lingual, palatal, mesial, distal, depth, implant sizes, final prosthetic emergence profile, osteotomy, drills, bone manipulation or expansion, surgical instrument position or angulation and depth, etc.) may be spatially planned in virtual/augmented or mixed reality prior to performance of a surgical procedure on a live patient, in some examples. For example, an SVSTP may be created based on the captured/scanned data. The SVSTP may include a virtual image of the surgical site, to allow for spatial planning of surgical procedures (e.g., dental implants, incisions, extractions, etc.), prior to actual performance of the surgical procedure(s) on a live patient. The surgeon can place an actual implant screw in the virtual site (SVSTP) to observe its fitting. At step 408, the SVSTP may be archived or stored as a file, for example, in a data repository for future live surgeries.

Figure 5:
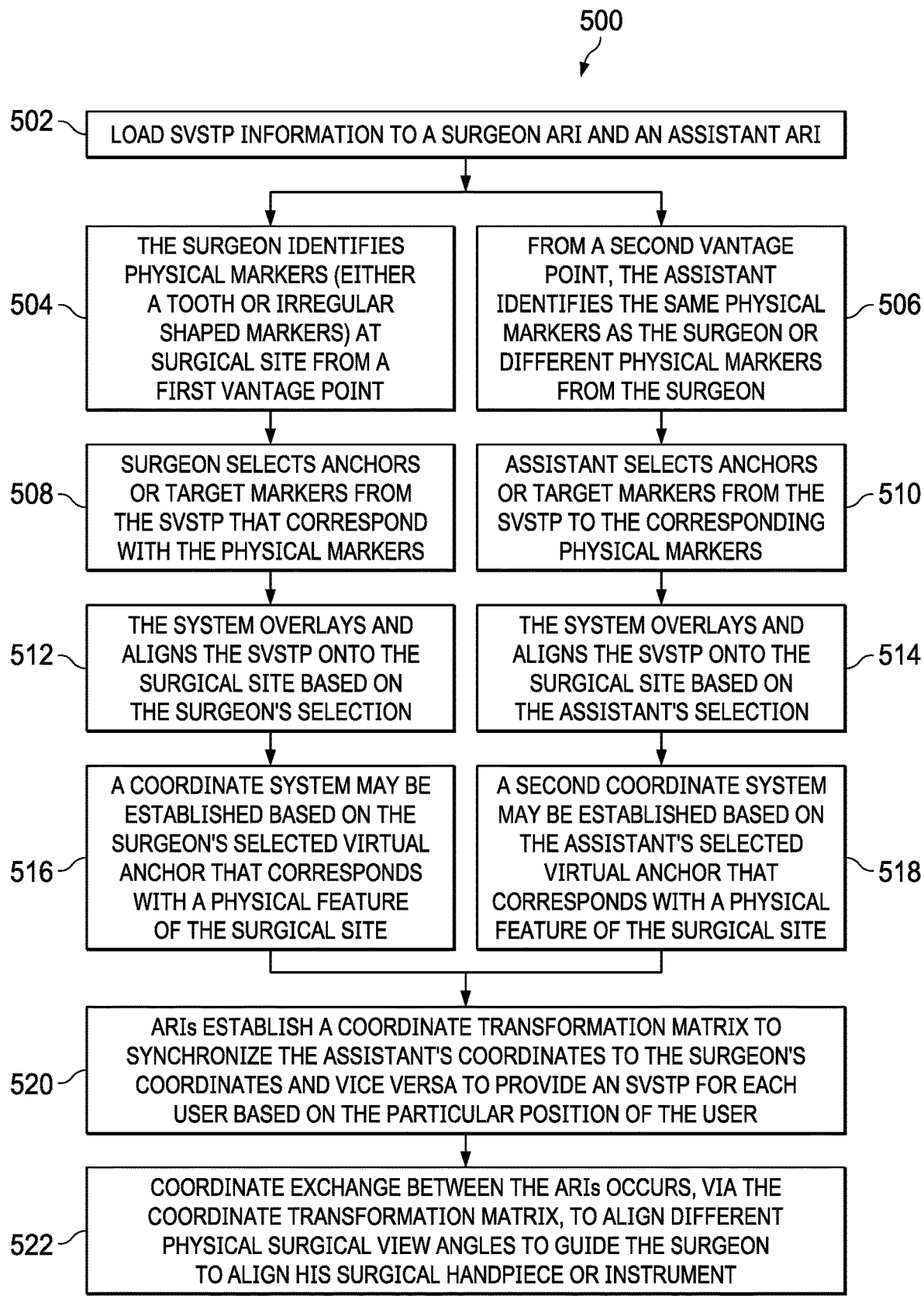
FIG. 5 illustrates a flow sequence for performing the AR assisted procedures, in accordance with embodiments of the present disclosure.

FIG. 5 illustrates a block diagram of a method in accordance with embodiments of the present disclosure. In block 502, the SVSTP may be loaded to a surgeon ARI and an assistant ARI. This step may be illustrated in FIG. 6, for example.

In block 504, a surgeon may identify physical rigid marker(s) (either a tooth or irregular shaped markers) at a procedure location. This step may be illustrated in FIG. 7, for example. In some examples, the physical rigid marker(s) may include a tooth's outline, anatomy, occlusal surface outline, transition, and/or temporary inserted special unique shape radio-opaque screw(s).

In block 506, an assistant may also identify physical rigid marker(s) at a procedure location. The assistant may identify the same or different physical rigid marker(s) from the surgeon. The selection of a physical rigid marker(s)/tooth depends on which tooth is visible to the assistant. Therefore, the assistant may select the same physical tooth as the surgeon at the physical surgical site of the patient or a different tooth or physical rigid marker(s) that is visible to the assistant.

Figure 9:
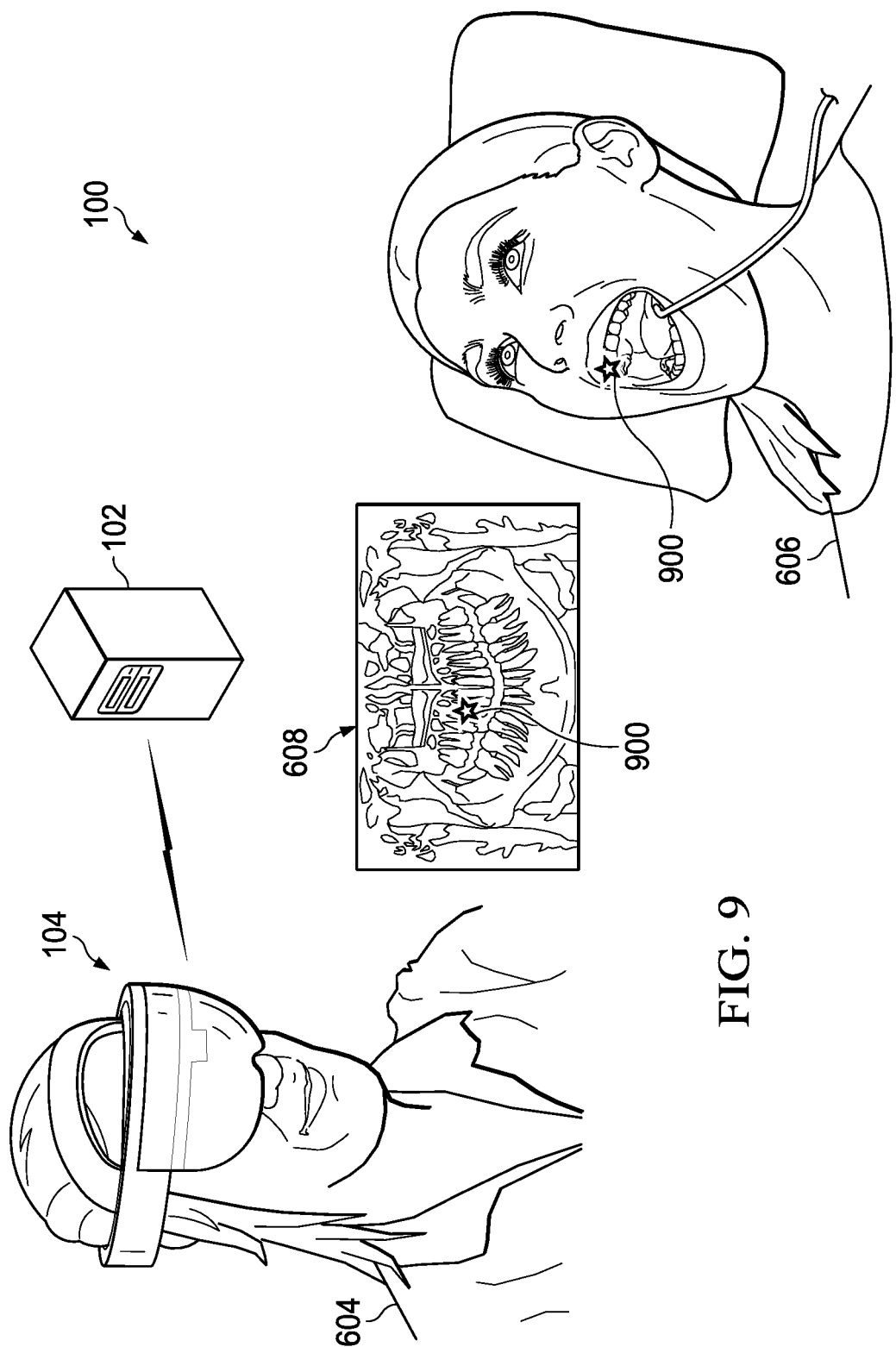
FIG. 9 illustrates establishing a coordinate system for a second ARI, in accordance with embodiments of the present disclosure.

This step may be illustrated in FIG. 9, for example. As noted previously, the physical rigid marker(s) may include a tooth's outline, anatomy, occlusal surface outline, transition, and/or temporary inserted special unique shape radio-opaque screw(s).

In block 508, the surgeon selects virtual anchors or target markers (e.g., irregular shaped virtual markers) in the SVSTP to correspond with physical rigid marker(s) at the surgical site. The target markers may include a tooth's outline/anatomy/occlusal surface outline, transition or temporary inserted special unique shape radio-opaque screw(s). This step may be illustrated in FIG. 8.

In block 510, the assistant may also select virtual anchors or target markers in the SVSTP that correspond with physical rigid marker(s) viewed from the assistant's spatial. This step may be illustrated in FIG. 9, for example.

In block 512, the system overlays and aligns the SVSTP onto the surgical site based on the surgeon's selection. In block 514, The system overlays and aligns the SVSTP onto the surgical site based on the assistant's selection.

In block 516, if the surgeon selected for example tooth #11 and or #20 in the virtual image (SVSTP), the same corresponding tooth #11 or #20 should be selected in the patient's live surgical site to allowing the surgeon ARI to overlay the images. The assistant at the same time can select the same tooth that the surgeon selected that is visible to her ARI from her view at the surgical site. If the tooth/teeth or the physical rigid marker(s) selected by the surgeon are not visible to her, she must select a different tooth/teeth. For example, if the assistant selects tooth #8 and #10 in the virtual image (SVSTP), the same corresponding tooth #8, and #10 are selected at the patient's surgical site as physical rigid marker(s) to allow her ARI to overlay the virtual image (SVSTP) precisely over the patient surgical site.

If the patient is complete edentulous, then irregular shape, radio-opaque screw needed to be inserted prior taking 3D x-ray to allow for treatment planning of the surgical site in SVSTP and to use an anatomical reference to align the virtual image (SVSTP) to the patient surgical site. The same corresponding markers in the virtual image must be selected in the patient surgical site. All physical rigid marker(s) whether the patient's tooth or teeth, tori, or insert irregular shape radio-opaque screw (for complete edentulous, or partial edentulous) must have the distinct irregular shape and must be captured by 3D x-ray, MRI, or CT scan.

In block 518, a second coordinate system may be established (e.g., a, b, c coordinates) based on the assistant's selected virtual anchors or target markers (e.g., irregular shaped virtual markers), for example, tooth #11 and/or #20, or transition or temporary inserted special unique shape radio-opaque screw(s) to correspond with the surgical site such as, for example, tooth #8 and/or #10, or transition or temporary inserted special unique shape radio-opaque screw(s). This step may be illustrated in FIG. 9 and may be similar to step 516, for example.

A coordinate transformation matrix is created when the ARIs select physical rigid marker(s) to overlay SVSTP to the physical surgical site. The precise superimposed of the overlaid SVSTPs, allows the ARIs to exchange coordinates when observing the physical surgical instrument. The coordinates exchange guides the physical surgical instrument to the precise planned surgical procedure in the SVSTP.

Surgeon's AR and Assistant's AR view at different angles, allowing the surgeon to calibrate his surgical instrument (surgical handpiece, osteotome) to the vertical axis of the planned dental implant position in the SVTSP. Multiple ARI views eliminate parallaxing and occlusion issues.

The SVSTP may include implant positions in the jaw with a vertical axis projected to allow the surgeon align his surgical instrument (surgical handpiece or osteotome) to align to the proper position in xyz planes. With the synchronization of the multiple ARI view at different angle at the time of surgery (after the virtual image (SVSTP) are aligned to the patient surgical site and the coordinates of transformation matrix of the multiple ARIs are established) the surgeon can align his surgical instrument with the vertical axis to perform the surgery without parallaxing and occlusion issues without requiring the surgeon to look away from the surgical location.

It should be noted that the 3D radiographic data (e.g., DICOM files, etc.) may be imported to the ARIs prior to surgery, the SVSTP may be manipulated and/or or planned in the surgeon's ARI and/or the assistant's ARI. The overlaying process occurs via selecting a tooth, teeth or physical rigid markers.

Figure 6:
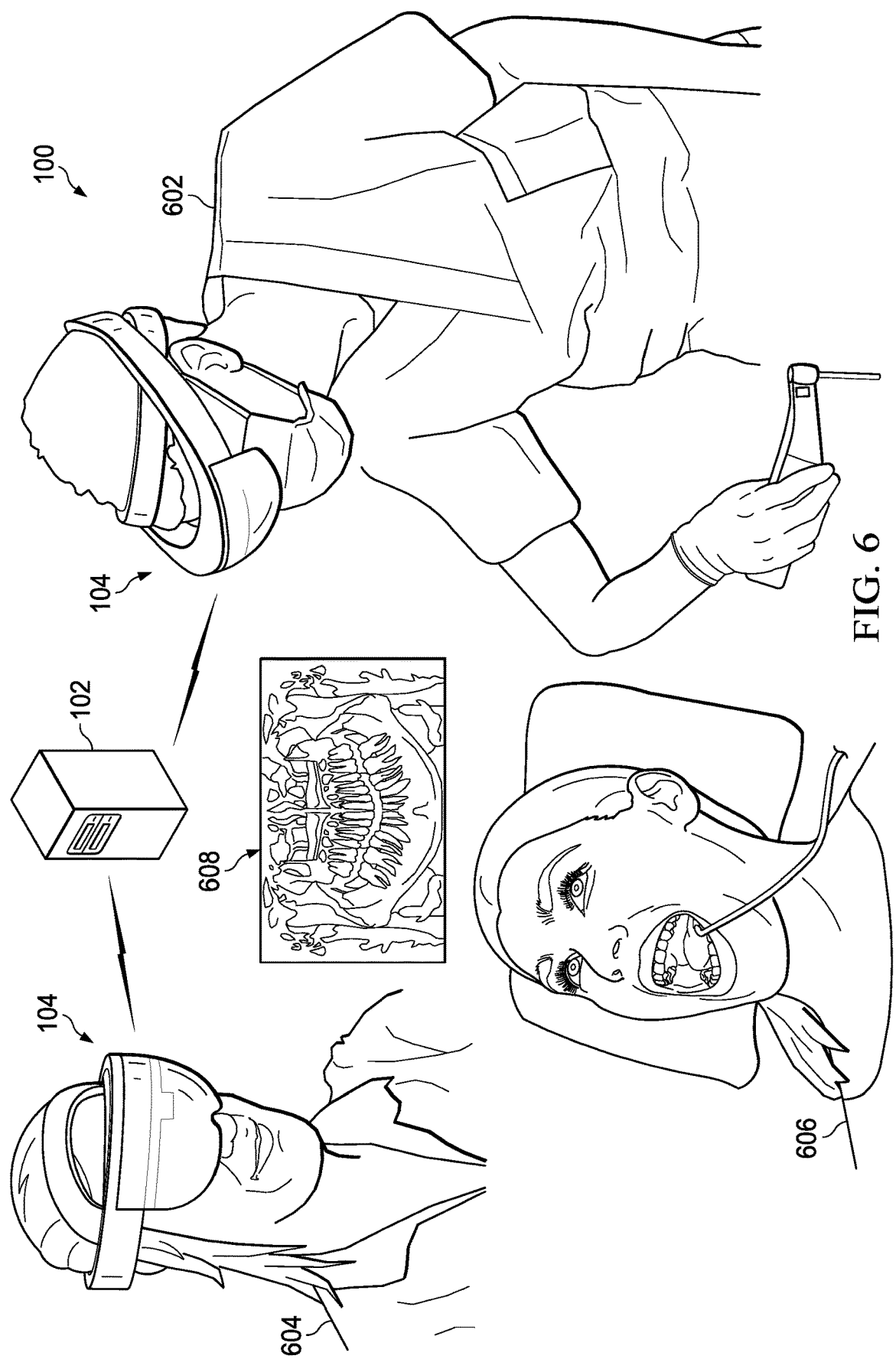
FIG. 6 illustrates loading the SVSTP onto multiple AR interfaces (ARIs), in accordance with embodiments of the present disclosure.

FIG. 6 illustrates the system 100 that is operable to load 3D SVSTP information onto ARIs 104, in accordance with embodiments of the present disclosure. A first user 602 and a second user 604 may be positioned on opposite sides of a patient 606, wearing first and second ARIs 104. There may be more than 2 ARIs, more ARIs will provide more viewing angles. The camera is mainly for tracking only. In order for it to be used as an ARI, one must wear it and intelligence/features must be added on to the camera to function as an ARI.

In some examples, an SVSTP 608 may be downloaded to an assistant's ARI 104 and a surgeon's ARI 104 via the computer 102.

Figure 7:
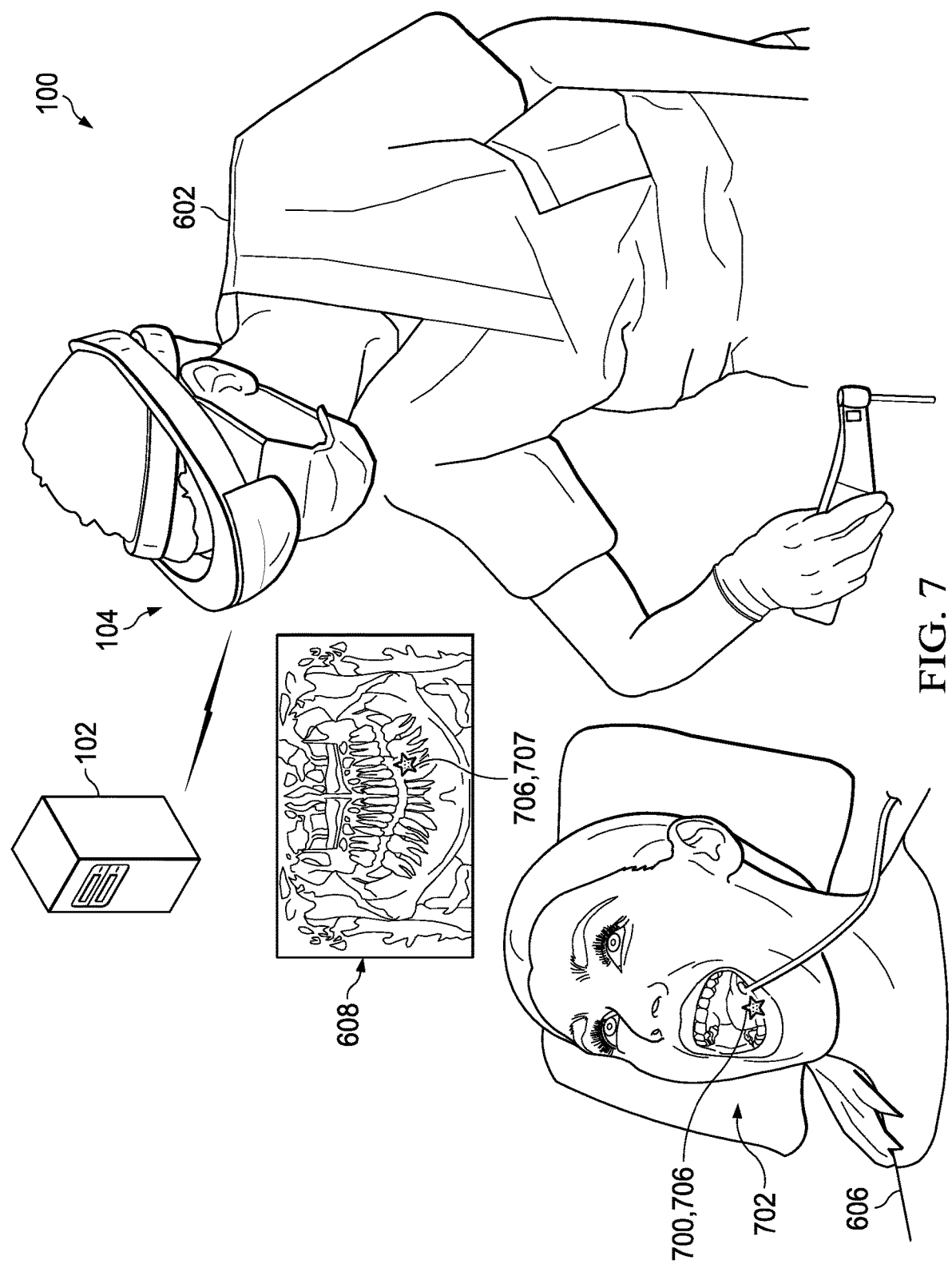
FIG. 7 illustrates identification of a physical marker at a live surgical site, in accordance with embodiments of the present disclosure.

FIG. 7 illustrates identification of a physical rigid marker(s) 700 at a live surgical site 702 with the system 100, in accordance with embodiments of the present disclosure. Using the ARI 104, for example, the first user 602 (e.g., the surgeon) may select a selection 706 which may include the physical rigid marker(s) 700 at the surgical site 702 such as a tooth or teeth and corresponding virtual feature 707 from the SVSTP 608.

Figure 8:
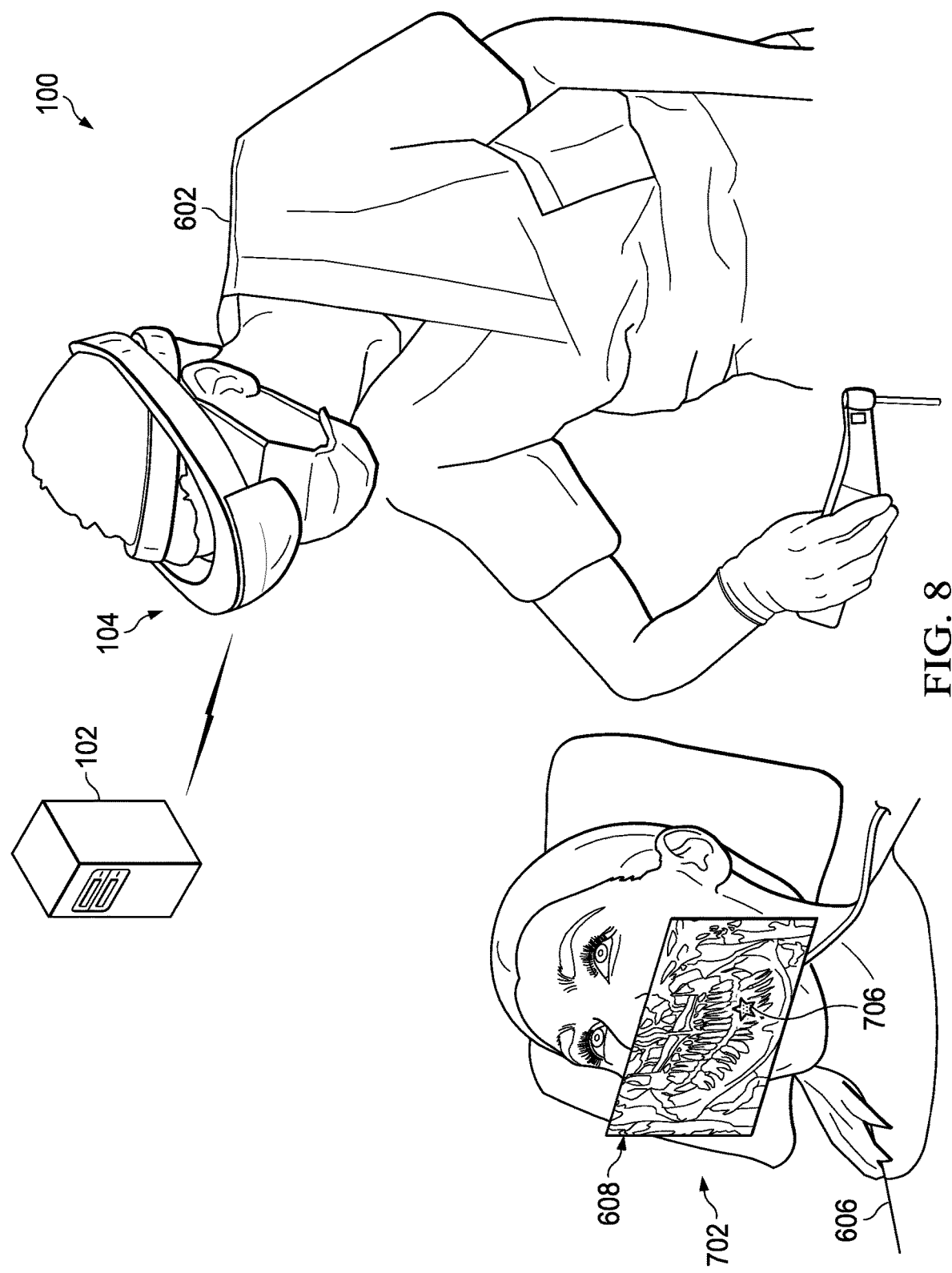
FIG. 8 illustrates establishing a coordinate system for a first ARI, in accordance with embodiments of the present disclosure.

FIG. 8 illustrates establishing a coordinate system with the system 100 for the first user 602 of the ARI 104, in accordance with embodiments of the present disclosure. Each ARI 104 may establish a coordinate system correlating the SVSTP 608 to the surgical site 702. Each ARI 104 may overlay the SVSTP 608 onto the surgical site 702 by aligning the selection(s) 706.

FIG. 9 illustrates the second user 604 identifying and selecting selection 900 that includes a virtual marker from the SVSTP 608 and corresponding physical rigid marker(s) with the system 100 and establishing a coordinate system with the system 100 for the second user 604 of the ARI 104, in accordance with examples of the present disclosure.

Figure 10:
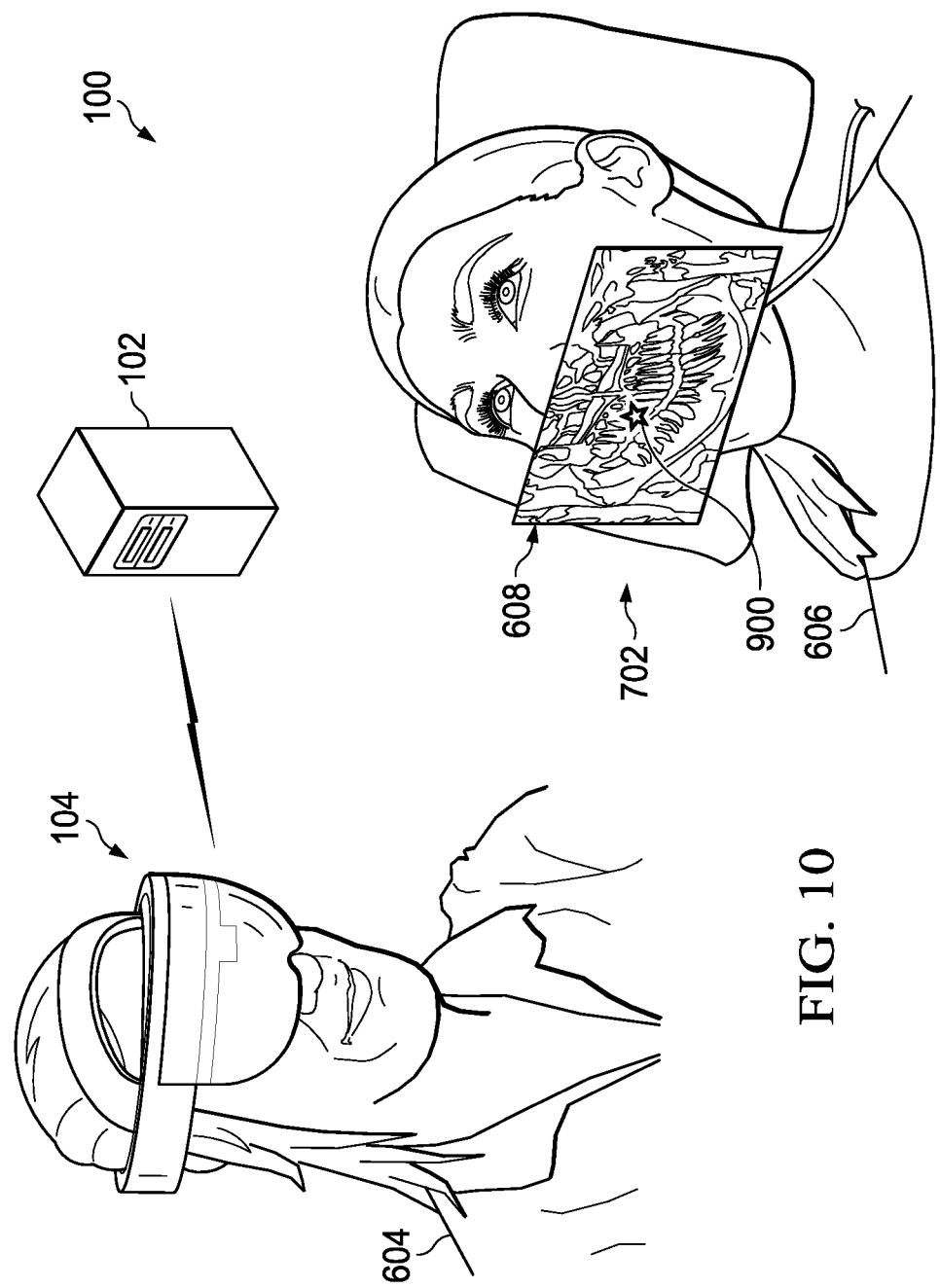
FIG. 10 illustrates overlaying a virtual image onto a surgical site, in accordance with embodiments of the present disclosure.

FIG. 10 illustrates overlaying the SVSTP 608 onto the surgical site 702 with the ARI 104 as viewed by the second user 604, in accordance with examples of the present disclosure. The ARI 104 may overlay the SVSTP 608 onto the surgical site based on the selection(s) 900.

Figure 11:
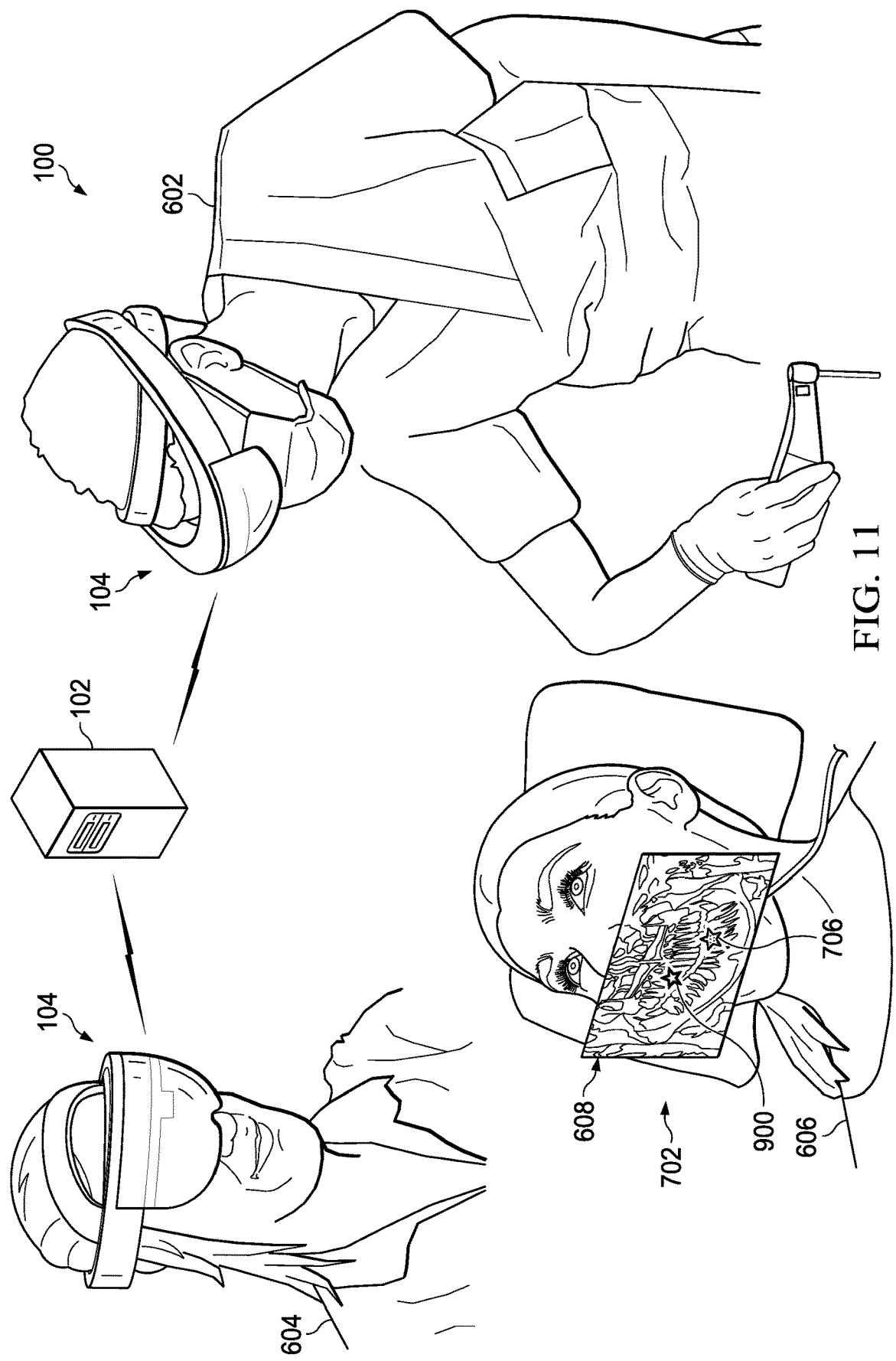
FIG. 11 illustrates establishing a coordinate transformation matrix to synchronize image data coordinates viewed from the multiple ARIs, in accordance with embodiments of the present disclosure.

FIG. 11 illustrates a superimposed SVSTP, in accordance with examples of the present disclosure. A coordinate exchange between the ARIs 104 may occur to align different physical surgical view angles. This may guide the surgeon's (e.g., the first user 602) surgical handpiece or instrument to perform precise dental implant osteotomy or surgical procedures according to the SVSTP 608 based on the selections 706 and 900, as noted previously. The coordinate transformation matrix may include a translation, for example, of X, Y, Z coordinates of the virtual image on the surgical site 702 and orientation/rotation angles of the virtual image on the surgical site 702.

Figure 12:
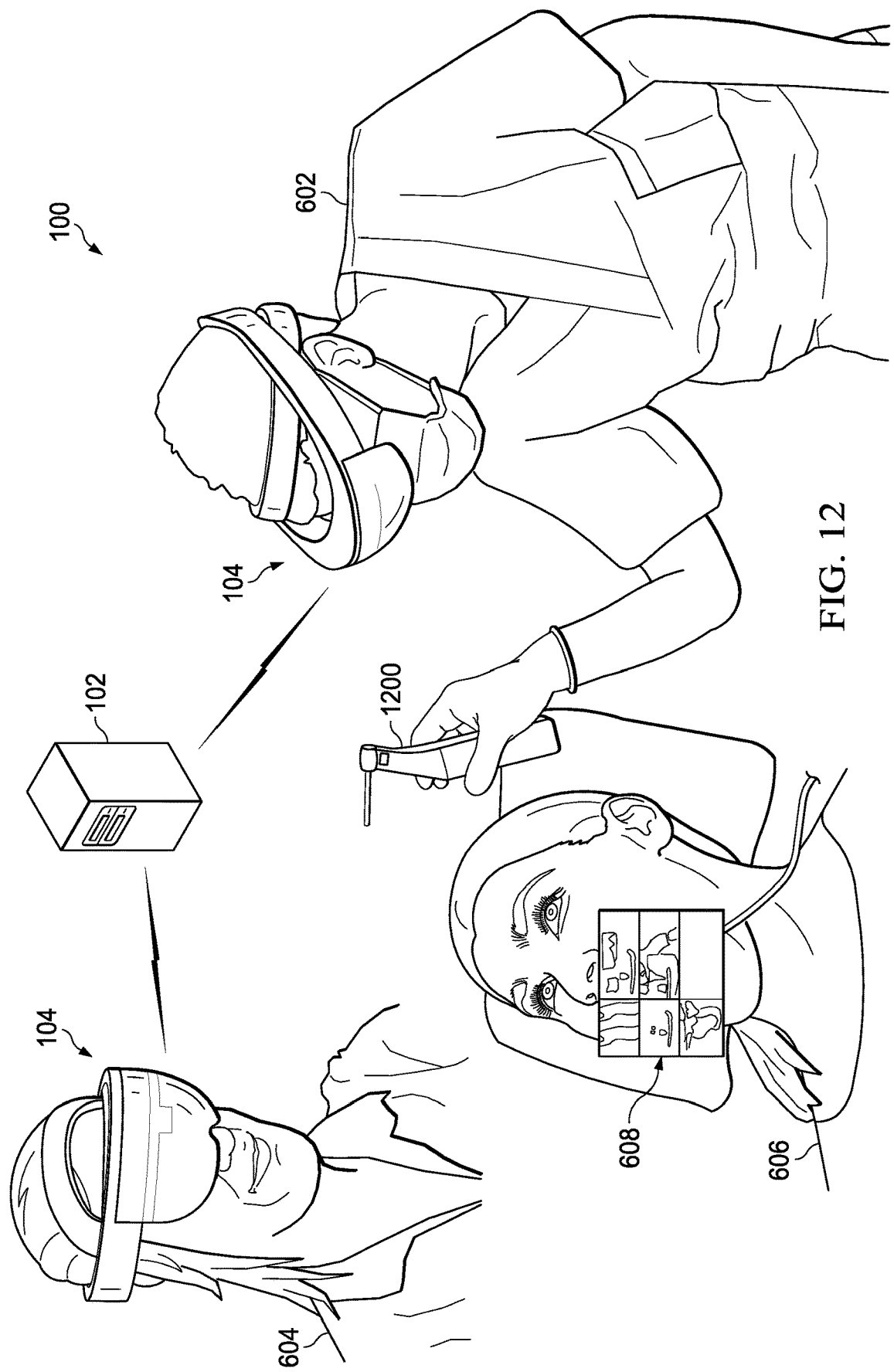
FIG. 12 illustrates a process of exchanging coordinate information from multiple ARIs, to allows the surgeon to calibrate the physical surgical instrument from multiple angles in order to align the physical surgical instrument to a correct angle as well as the drilling location to avoid parallaxing and occlusion issues, in accordance with examples of the present disclosure.

FIG. 12 illustrates aligning a surgical handpiece or instrument 1200 to perform precise dental implant osteotomy or surgical procedure, according to the SVSTP 608, in accordance with examples of the present disclosure. The ARI 104 may allow the user 602 (surgeon) to see the physical surgical instrument 1200 directly and unobstructed. Synchronization of the ARI(s) 104 at different physical surgical view angles may guide the surgeon to calibrate his instrument 1200 to perform precise dental implant osteotomy or surgical procedure according to the SVSTP 608 with an unobstructed view with no parallax effect. The nature of the ARI allows overlaying a virtual image (SVSTP) onto the patient's physical surgical site, enabling the surgeon to see the outline of a hidden view or occlusion view.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. An augmented reality (AR) assisted surgical system comprising:
   a three-dimensional spatial virtual surgical treatment plan (SVSTP) for mixed or virtual reality; and
   multiple AR interfaces (ARIs), including a first ARI and a second ARI, at least the first ARI and the second ARI configured to overlay the SVSTP onto a surgical site to generate an overlaid SVSTP viewed from the first ARI and an overlaid SVSTP viewed from the second ARI, wherein the ARIs are positioned at different angles and are configured to exchange three-dimensional coordinate information with each other, wherein the exchanged coordinate information is used to align different surgical view angles to superimpose at least the overlaid SVSTP viewed from the first ARI with the overlaid SVSTP viewed from the second ARI to generate a superimposed SVSTP, which is used to display information on at least the first ARI to guide a surgical instrument in three dimensions, and to provide an unobstructed view of the surgical site and reduce parallax and occlusion errors during surgery.

2. The system of claim 1, further comprising a camera in communication with the ARIs, the camera dynamically positionable to reduce viewing obstruction at the surgical site.

3. The system of claim 1, wherein at least one of the ARIs comprises a face shield, wherein the face shield comprises a display configured to display the SVSTP.

4. The system of claim 1, wherein the coordinate information comprises less than 1 kilobyte of coordinates without images.

5. The system of claim 1, wherein at least the first and the second ARIs are operable to synchronize surgical images and surgical procedures.

6. The system of claim 5, wherein at least one of the ARIs is operable to project synchronized surgical images and surgical procedures onto another ARI for teaching purposes.

7. The system of claim 1, wherein at least the first and second ARIs are configured to utilize a coordinate transformation.

8. The system of claim 1, wherein the SVSTP comprises virtual markers.

9. The system of claim 8, wherein the surgical site comprises physical rigid markers.

10. The system of claim 9, wherein the virtual markers are positioned to overlay corresponding ones of the physical rigid markers.

11. The system of claim 9, wherein the physical rigid markers comprise anatomical structures.

12. The system of claim 9, wherein the physical rigid markers comprise radiographical markers.

13. The system of claim 1, wherein the SVSTP is pinned to the surgical site.

14. A method for performing augmented reality (AR) assisted surgery, the method comprising:
loading a three-dimensional spatial virtual surgical treatment plan (SVSTP) onto multiple ARIs, including a first ARI and a second ARI;
positioning the first ARI and the second ARI at different angles to a surgical site during surgery;
identifying virtual and one or more corresponding physical rigid markers with at least the first and second ARIs based on the SVSTP;
exchanging three-dimensional coordinate information between at least the first and second ARIs;
overlaying the SVSTP onto the surgical site viewed from at least the first ARI and the second ARI to generate an overlaid SVSTP viewed from the first ARI and an overlaid SVSTP viewed from the second ARI;
using the exchanged coordinate information to align different surgical view angles to superimpose at least the overlaid SVSTP viewed from the first ARI with the overlaid SVSTP viewed from the second ARI to generate a superimposed SVSTP; and
displaying information based on the superimposed SVSTP on at least the first ARI to guide a surgical instrument in three dimensions, and to reduce parallax and occlusion issues during surgery.

15. The method of claim 14, further comprising establishing a coordinate system for the ARIs.

16. The method of claim 15, further comprising tracking the surgical site with a camera.

17. The method of claim 16, further comprising establishing a coordinate transformation to exchange coordinates.

18. The method of claim 17, further comprising placing markers at the surgical site.

19. The method of claim 14, further comprising selecting virtual markers from the SVSTP with at least the first and second ARIs.

20. The method of claim 19, further comprising selecting physical markers at the surgical site that correspond with the virtual markers.

* * * * *